United States Patent [19]
Violante et al.

[11] Patent Number: 5,741,522
[45] Date of Patent: Apr. 21, 1998

[54] ULTRASMALL, NON-AGGREGATED POROUS PARTICLES OF UNIFORM SIZE FOR ENTRAPPING GAS BUBBLES WITHIN AND METHODS

[75] Inventors: Michael R. Violante, Pittsford; Kevin J. Parker, Rochester, both of N.Y.

[73] Assignee: University of Rochester, Rochester, N.Y.

[21] Appl. No.: 460,963

[22] Filed: Jun. 5, 1995

Related U.S. Application Data

[62] Division of Ser. No. 384,193, Feb. 6, 1995, which is a continuation of Ser. No. 106,966, Aug. 16, 1993, abandoned, which is a continuation of Ser. No. 725,983, Jul. 5, 1991, abandoned.

[51] Int. Cl.$^6$ ........................................... A61K 9/14
[52] U.S. Cl. .................. 424/489; 128/662.2; 210/639; 210/709; 210/729; 423/495; 424/9.5; 424/9.51; 424/9.52; 424/495; 514/410; 514/951; 514/965; 560/45; 562/455
[58] Field of Search ..................... 424/9.5, 9.51, 424/9.52, 489, 492; 128/662.2; 23/305; 210/639, 709, 729; 269/9; 502/8; 423/495; 514/410, 951, 965; 562/455; 560/45

[56] References Cited

U.S. PATENT DOCUMENTS 4,997,454  3/1991  Violante et al. ........................... 23/205

*Primary Examiner*—Shailendra Kumar
*Attorney, Agent, or Firm*—Spencer & Frank

[57] ABSTRACT

This invention relates to the preparation, composition and applications of suspensions of ultra-small, substantially non-aggregated, non-crystalline particles of predetermined uniform size which, when suspended in a liquid, contain entrapped gaseous bubbles. These gaseous bubble particles are prepared by simultaneous co-precipitation of two compounds. In accordance with the present invention, the two compounds chosen for co-precipitation are such that one is substantially more soluble than the other in a given vehicle. When this vehicle is used for washing the co-precipitated particles, part of the soluble material is dissolved leaving a porous matrix. The porous particles then are dried and stored. The porous particles, which can be resuspended immediately prior to use, contain entrapped gas in the evacuated crevices or pores which is not displaced for a period of time because of surface tension of the suspending vehicle. These ultrasmall, substantially non-aggregated porous particles therefore can be used to advantage as ultrasound contrast agents as well as other applications.

33 Claims, 4 Drawing Sheets

ULTRASMALL, NON-AGGREGATED POROUS PARTICLES OF UNIFORM SIZE FOR ENTRAPPING GAS BUBBLES WITHIN AND METHODS

This is a divisional of application(s) Ser. No. 08/384,193 filed on 6 Feb. 1995, which is a File Wrapper Continuation of Ser. No. 08/106,966 filed on 16 Aug. 1993 now abandoned, which is a File Wrapper Continuation of Ser. No. 07/725,983 filed 5 Jul. 1991, now abandoned.

FIELD OF THE INVENTION

The present invention relates to ultrasmall, substantially non-aggregated porous particles of predetermined uniform size which, when reconstituted contain entrapped gas bubbles. The ultrasmall porous particles are suitable for use as fillers and the like, and as ultrasound contrast agents when suspended in a suitable ultrasound liquid. The present invention further relates to methods of making and using such ultrasmall, uniform porous particles.

BACKGROUND OF THE INVENTION

Particles of compounds having low solubility in a dispersing medium are commonly used in a wide variety of applications, including pharmaceuticals, ceramics, paints, inks, dyes, lubricants, pesticides, insecticides, fungicides, fertilizers, chromatography columns, cosmetics, lotions, ointments, and detergents. Aqueous dispersions of particles are used in many cases to avoid hazards such as flammability and toxicity associated with organic solvents. Such dispersions typically have a broad range of particle size.

In many cases, product performance is improved by controlling the particle size distribution. In general, smaller particles of a compound provide a more uniform dispersion and will dissolve faster than larger particles of the same compounds. Control of particle size is, therefore, important in controlling the rate of solubilization.

Many drugs have been formulated as particles for sustained-release following oral, aerosol, subcutaneous, intramuscular, or other routes of administration. Particle size is one important factor affecting the release rate of these drugs. Those skilled in the art can discern other examples for using particle size to control product performance for the substances listed above.

Drugs that are insoluble in water can have significant benefits when formulated as a stable suspension of particles of less than three microns diameter. In this particulate form, the drug can be injected intravenously, circulate in blood, and be preferentially accumulated in, for example, the reticuloendothelial system, where it can facilitate normal reticuloendothelial functions such as detoxification. Alternatively, the drug can reside in the reticuloendothelial cells where it is stored until solubilized or metabolized into an active form which circulates in blood to other tissues for efficacy. This "slow" release of active drug can provide more constant drug concentrations in plasma over a period of hours, days, weeks, or months, resulting in improved therapeutic efficacy. Biodegradable particles which are radiopaque or labelled with a radioisotope are useful for diagnostic imaging of organs, such as liver and spleen, with high concentrations of fixed reticuloendothelial cells.

Solid biodegradable particles also can be useful for diagnostic ultrasound imaging of the liver and spleen with ultrasound. These particles can be effective if they have a density significantly higher than surrounding tissue, thereby producing an impedance mismatch responsible for backscatter enhancement. Since tumors and other lesions generally do not contain these fixed reticuloendothelial cells, particles are not accumulated in these lesions so only tissue parenchyma backscatter is enhanced creating a larger difference in echogenicity between parenchyma and lesion thereby facilitating lesion detection and diagnosis by ultrasound. See, for example, Parker, K. J. et al.: *Ultrasound in Med. & Biol.*, 13(9):555–566 (1987).

By far the simplest form of ultrasound contrast agents is free gas bubbles. Such bubbles may preexist in the liquid vehicle, or may be introduced via cavitation during the injection phase. Whatever the mechanism may be, it appears that many liquids, when rapidly injected into ducts or vessels, are capable of generating a quantity of air bubbles which may produce sufficient echoes to cause partial or complete intraluminal sonographic opacification.

The first report on the use of free gas bubbles appears to be that of Gramiak, R. and Shah, P.M.: *Investigative Radiology*, 3:356–366 (1968). They reported that they obtained anatomic validation of the aortic origin of cardiac echoes by means of direct physiological saline injection during continuous echocardiographic recording. The injection produced a cloud of echoes which was delineated by the parallel signal of the aortic root. See also, for example, U.S. Pat. No. 4,276,885. Kremkau, F. W. et al.: *Am. J. Roentgend.*, 3:159 (1968) also reported that they obtained intracardiac echoes from saline injection and from injection of autologous blood. They demonstrated that air bubbles may be generated during the injection process itself. Ziskin, M. C. et al.: *Investigative Radiology*, 7:500–505 (1972) reported using a variety of liquids, such as renografin, carbonated water, and ether (which boils at body temperature) to demonstrate the presence of echoes in all cases, detected by enhanced Doppler signals from arteries. In recent years, numerous investigators such as Chiang, C. W. et al.: *Chest*, 89(5):723–726 (1986), Rizayev, M. N. and Azatyan, T. S.: *Heart J.*, 10(6):1308–1310 (1985), Feinstein, S. B. et al.: *J. Am. Coll. Cardiol.*, 3(1):14–20 (1984), Konodo, S. et al.: *J. Am. Coll. Cardiol.*, 4:149–156 (1984), Ten-Cate, F. J. et al.: *J. Am. Coll. Cardiol.*, 3(1):21–27 (1984), Maurer, B. et al.: *Circulation*, 69(2):418–429(1984), Armstrong, W. F. et al.: *J. Am. Coll. Cardiol.*, 2(1):63–69 (1983), Tei, C. et al.: *J. Am Coll. Cardiol.*, 3(1):39–46 (1984), Armstrong, W. F. et al.: *Circulation*, 66(1):166–173 (1982), Meltzer, R. S. et al.: *Br. Heat J.*, 44(4):390–394 (1980a), Meltzer, R. S. et al.: *J. Clin. Ultras.*, 9(3):127–131 (1981), Wise, N. K. et al.: *Circulation*, 63(5):1100–1103 (1983), Meltzer, R. S. et al.: *Ultrasound Med. Biol.*, 6(3):263–269 (1980b), have reported the use of indocyanine green for opacification of the common bile duct in cholangiography. Presumably, microscopic air bubbles contained in the liquid or generated during the injection phase is responsible for the observed effects. Meyer-Schwickerath, M. and Fritzsch, T.: *Ultraschall Med*, 7:34–36 (1986) have reported urologic applications of a new commercial agent which incorporates solid particles as microbubble carriers.

While free gas bubbles are extremely efficient scatterers of sound energy, their utility is limited by the fact that they are effectively removed by the lungs or by pressure changes in the heart. Thus, it is impractical to use microbubbles to elicit contrast in the soft tissue via venous injection.

In an effort to overcome some of the limitations of free gas bubbles, encapsulated gas bubbles were manufactured and injected directly into the carotid artery in tumor bearing rabbits. See Carroll, B. A. et al.: *Investigative Radiology*, 15(3):260–266 (1980). These consisted of nitrogen gas trapped in 80 micron gelatin capsules. Carroll et al. report ultrasonic enhancement of tumor rims in rabbits with VX2 carcinoma. The large size of these particles did not allow their administration in the peripheral circulation. Unfortunately, the manufacturer of small (2–3 microns), gas filled capsules which could clear the lungs is difficult due to the extreme thinness of the capsule wall through which gas diffuses.

As another alternative, U.S. Pat. No. 4,442,843, U.S. Pat. No. 4,657,756 and U.S. Pat. No. 4,681,119, disclose the use of aggregates as carriers of gas to produce microbubbles in blood to alter the transmission characteristics thereof to electromagnetic and sonic waves transmitted therethrough. Unfortunately, because the aggregates are of such a large size, i.e., on the order of between about 20–250 microns, it is difficult if not impossible for such aggregates to travel past the lungs and heart, thereby limiting their usefulness as ultrasound contrast agents. In addition, because the solid materials from which the aggregates are formed will generally solubilize in body fluids over a short period of time, their ability to enhance ultrasound images in the lungs and heart is short-lived. Moreover, the individual particles from which the aggregates are formed have little bubble generating capacity in their unaggregated form.

Consequently, there is a demand in the ultrasound industry for a contrast agent which offers enhanced gas bubble echogenicity with good long-term stability for arterial and organ ultrasound image enhancement following intravenous injection.

SUMMARY OF THE INVENTION

In brief, the present invention alleviates and overcomes certain of the above-mentioned problems and shortcomings of the present state of the art through the discovery of novel ultrasmall, substantially non-aggregated, non-crystalline porous particles of substantial uniform size which, when reconstituted, contain entrapped gas bubbles, and methods of making and using same.

The novel ultrasmall, non-aggregated porous particles of the instant invention are uniquely suited for use as ultrasound image enhancers when reconstituted with suitable physiologically acceptable liquids. Quite amazingly, the novel ultrasmall, non-aggregated porous particles provide unique gas bubble echogenicity with good long-term stability for arterial and organ ultrasound image enhancement following intravenous injection. Even more amazingly, the ultrasmall porous particles of the instant invention are able to accomplish this without having to form aggregates in order to develop microbubbles to enhance ultrasound imaging.

It has also been discovered, and quite surprisingly, that the novel ultrasmall, non-aggregated porous particles of the instant invention produce enhanced and long-term ultrasound back scatter as a result of gas bubbles, such as air or helium bubbles, being trapped within their solid matrices or pores when they are suspended in a liquid. It is believed that the solid matrices or pores provide the stability for the unique sustained echogenicity which heretofore has not been achieved by the ultrasound contrast agents presently available. And, because the novel ultrasmall porous particles of the instant invention have virtually no tendency to aggregate, they are uniquely suited for use as contrast agents to enhance ultrasound images in the blood vessels and soft tissue or organs throughout an animal. In other words, because the novel ultrasmall porous particles have the capacity to circulate throughout the body of an animal, their suitability as ultrasound contrast agents greatly extends beyond the lungs and heart into, for example, the liver, spleen, heart myocardium, kidney, brain and the like.

In accordance with the present invention, the ultrasmall, porous particles of the instant invention are believed to be stable at ambient temperatures, have little to no tendency to aggregate, and are non-toxic and physiologically acceptable when introduced into the bloodstream of living beings, such as humans. The size of the ultrasmall, porous particles of the present invention typically range from up to about 10 microns, and preferably from about 0.01 microns to about 5.0 microns, and more preferably from about 0.1 microns to about 2.0 microns.

Preferred ultrasmall, substantially non-aggregated, non-crystalline porous particles of the instant invention are iodipamide ethyl ester particles having a substantially uniform mean diameter on the order of, for example, about 0.5 microns and the ability to entrap gas bubbles within their pores after resuspension in a liquid vehicle.

In accordance with a further feature of the instant invention, the ultrasmall porous particles of substantially uniform size are made by, first, preparing a solution of two separate solid compounds in a suitable solvent for the two compounds, second, infusing a precipitating liquid into the solution at a temperature between about −50° C. and about 100° C. and at an infusion rate of from about 0.01 ml/min. to about 3000 ml/min. per unit volume of 50 ml, the two solid compounds having essentially little solubility in the precipitating liquid and the solvent being miscible in the precipitating liquid, so as to produce a suspension of precipitated solid compounds in the form of substantially non-aggregated particles with a substantially uniform mean particle diameter selected from the range of up to about 10 microns, such that the particle size is directly related to the solution temperature and inversely related to infusion rate, third, separating the co-precipitated particles from the solvent, and, fourth, washing the co-precipitated particles with a washing liquid which serves to selectively solubilize and remove the second compound as well as any remaining residual solvent thereby producing particles consisting of a porous matrix consisting of only, or mostly, the first compound. The ultrasmall "porous" particle suspension is then dried to remove as much moisture as possible and to permit the porous particles to entrap gas within their porous matrices upon suspending the particles in liquid vehicles. The ultrasmall, porous particles of the instant invention are much less dense than pure solid particles formed alone following the same procedure.

It should be appreciated by those versed in this art that when the dried ultrasmall, porous particles are reconstituted or suspended in a suitable liquid, they are completely redispersed, but now a small amount of air or other gas such as helium has been entrapped in the particle crevices or pores where the second compound initially was present. The crevices or pores with entrapped air is believed to remain for several hours, even after resuspension in a liquid vehicle. Moreover, it is believed that because the crevices or pores are so small, the surface tension of the suspending liquid does not permit rapid filling. Consequently, such reconstituted suspensions are uniquely suited for use as ultrasound contrast materials because the echogenic gas bubbles trapped within the solid porous particles are stabilized, even against pressure changes in the heart which typically destroys other competitive ultrasound contrasting agents currently available.

In practicing the methods to produce the ultrasmall porous particles of the instant invention, a preferred weight ratio of the more soluble to the less soluble compound in the washing solution is from about 2:1 up to about 10:1. In addition, the amount of the more soluble compound dissolved and removed during the washing of the particles can be from about 10% to about 100% of the amount of the more soluble compound present in the particles after precipitation, but before washing.

In one preferred embodiment, the less soluble compound in the washing solution is iodipamide ethyl ester (IDE) and the more soluble compound in the washing solution is iodipamic acid (IDA). The precipitating liquid is water at about pH 5 and the washing liquid is aqueous 0.1% PVP at about pH 11. When washing the co-precipitated particles in accordance with the methods of the instant invention, washing can be continued until the solution remains basic after contact with the particles indicating that all IDA has been removed.

In accordance with a further feature of the present invention, the ultrasmall, porous particles may be coated with various substances, such as human serum albumin or selected antibodies, to alter the surface properties of the particles to improve, for example, their biocompatibility or their ability to target a desired site.

Accordingly, it can now be appreciated by those versed in this art that the present invention provides a solution to the ultrasound art that has long sought to overcome the shortcomings associated with the ultrasound contrast agents and methods available heretofore.

The above features and advantages of the present invention will be better understood with reference to the FIGS., Detailed Description and Examples set out hereinbelow. It will also be understood that the ultrasmall, porous particles and methods of this invention are exemplary only and are not to be regarded as limitations of this invention.

BRIEF DESCRIPTION OF THE FIGS.

Examples of the present invention will now be more fully described, with reference to the accompanying FIGS., wherein:

FIG. 1 depicts raw backscatter values (RMS) of in vitro bubble/IDE particle suspensions at 5.2 mg/ml plotted versus the weight ratio of iodipamic acid (IDA) to iodipamide ethyl ester (IDE) in a formulation mixture before dissolving away the IDA. These data demonstrate increased echogenicity (porosity) with higher ratios of IDA/IDE;

FIG. 2 depicts raw backscatter values (RMS) of in vitro bubble/IDE particle suspensions at 5.2, 9.1 and 13.1 mg/ml plotted versus time after mixing with bovine plasma. These data demonstrate increased backscatter with increased particle concentration. These data also demonstrate the extremely long persistence of this backscatter after mixing with bovine plasma compared with other bubble agents which survive only seconds to minutes;

FIG. 3 depicts raw backscatter values (RMS) of in vitro bubble/IDE particles at 5.2 mg/ml and standard solid IDE particles at 12.2 mg/ml plotted versus time. These data demonstrate the increased echogenicity obtained with bubble/IDE particles compared with that for solid IDE particles. This enhanced echogenicity is observed even though the bubble/IDE particles are at less than half the concentration of the solid IDE particles;

Figure 6:
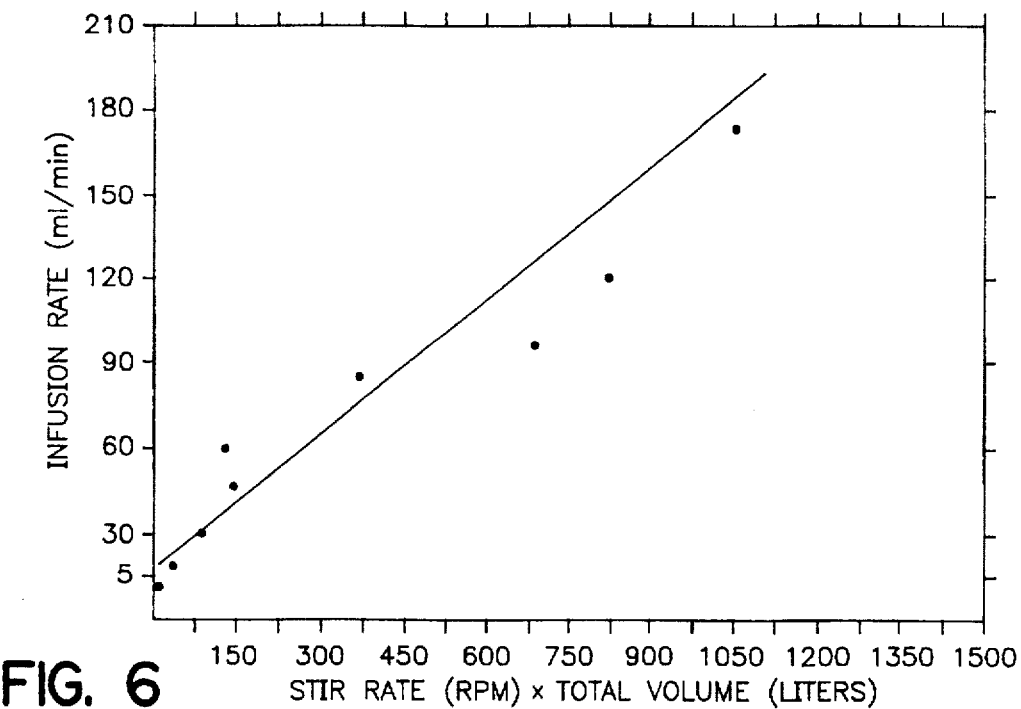
Figure 7:
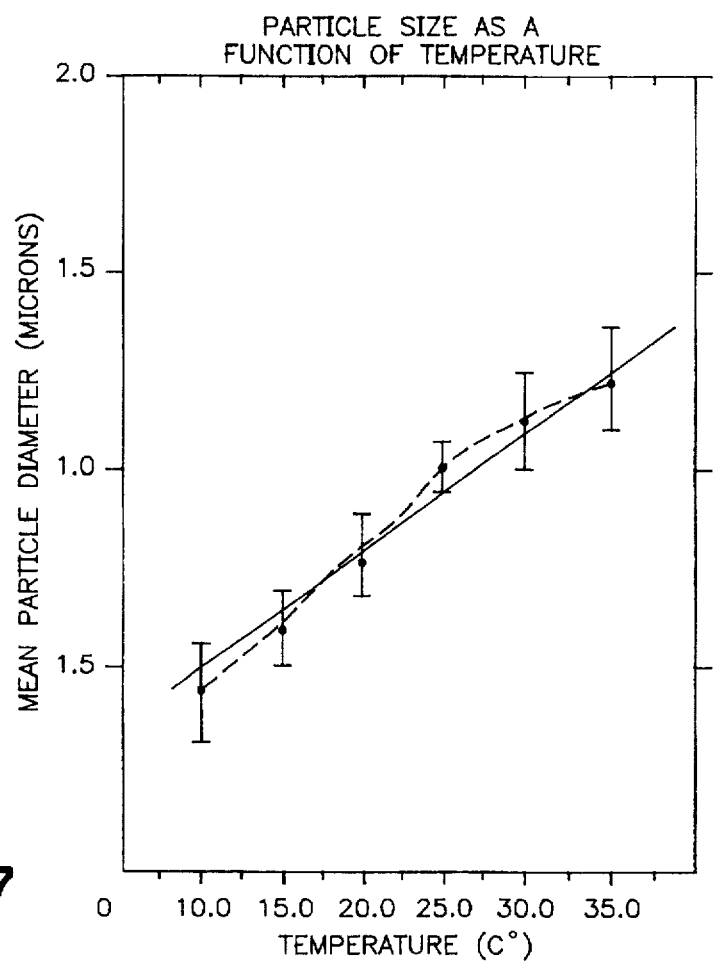
Figure 8:
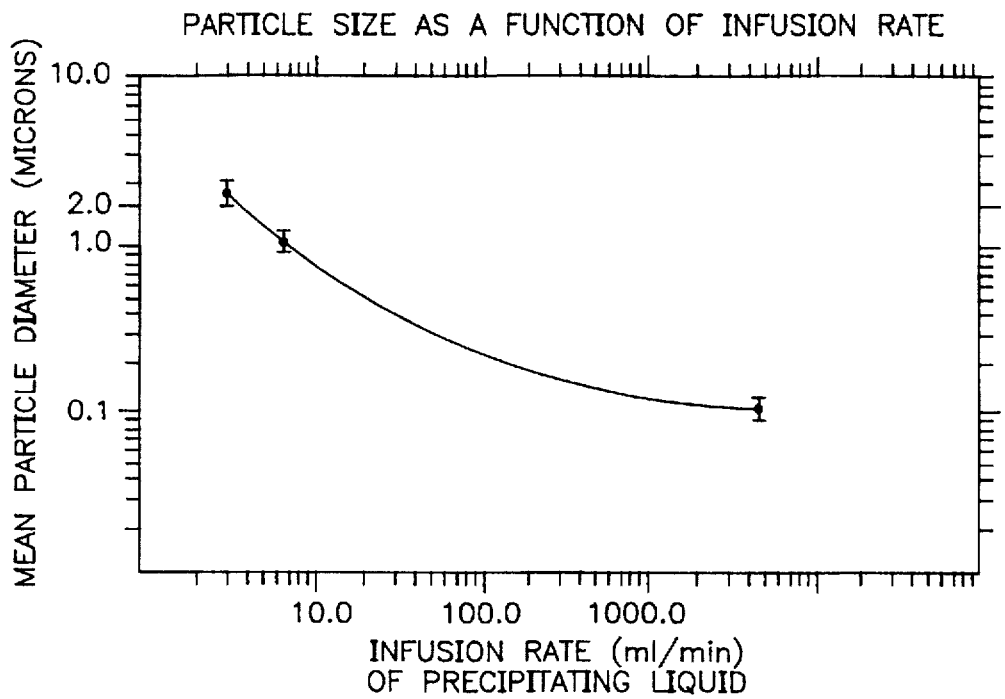
Figure 9:
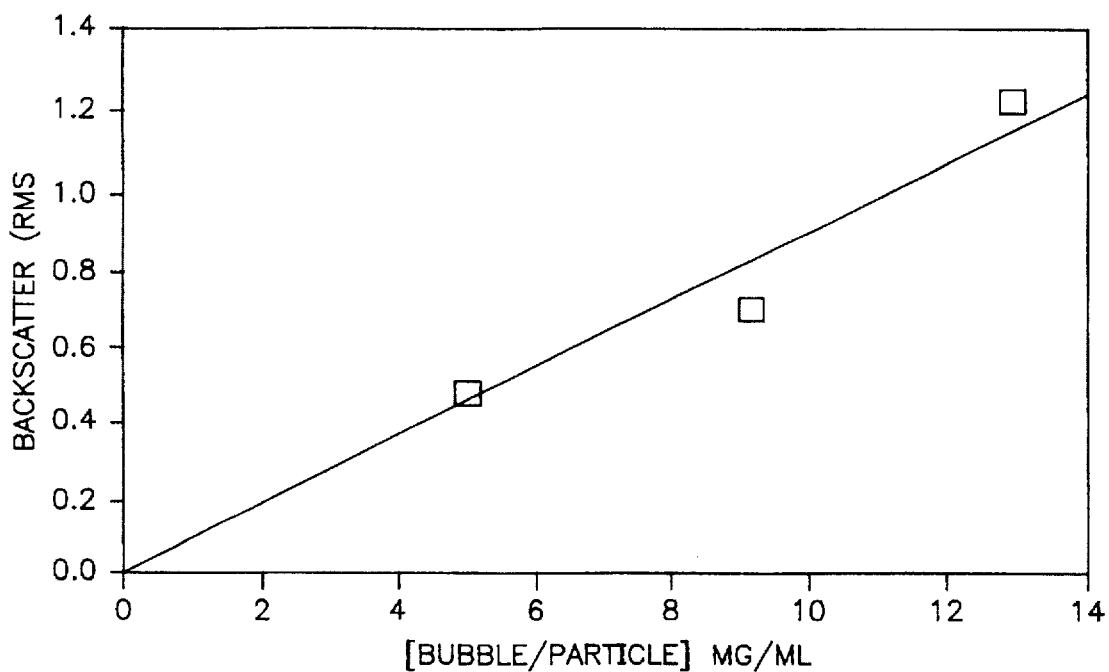

FIG. 6 is a graph of infusion rate (ml/min.) (of aqueous precipitating liquid) as a function of the product of stir rate (rpm) and total volume (liters) of the organic solution at a constant temperature; the relationship: aqueous infusion rate (ml/min.)=23+0.14 [stir rate (rpm)×volume organic solution (1)] defines the parameters for production of iodipamide ethyl ester particles of one micron diameter at a constant temperature (4° C.) and in dimethylsulfoxide/ethanol;

FIG. 7 is a graph showing iodipamide ethyl ester particle size as a function of temperature at a constant ratio of infusion rate of aqueous precipitating liquid to [stir rate (rpm)×volume of organic solution];

FIG. 8 is a graph demonstrating the effect on particle size of varying the infusion rate of aqueous precipitating liquid at constant temperature and stirring rate of an iodipamide ethyl ester solution; and FIG. 9 depicts raw backscatter values (RMS) of in vitro bubble-IDE particle suspensions at 5.2 mg/ml. These data demonstrate that backscatter increases linearly with concentration.

DETAILED DESCRIPTION OF THE INVENTION

By way of illustrating and providing a more complete appreciation of the present invention and many of the attendant advantages thereof, the following detailed description is provided concerning the novel ultrasmall, substantially non-aggregated, non-crystalline porous particles, and methods of making and using such particles.

This invention concerns the preparation of non-aggregated porous particles of a predetermined uniform size. One aspect of the invention concerns the preparation of uniform particles of a predetermined size in a vehicle in which the concentration of the compound in the vehicle is greater than the solubility of the compound in that vehicle. The particles are formed by a carefully controlled precipitation of the compound into a suitable precipitating liquid from a solvent in which the compound is soluble.

A second aspect of this invention is the simultaneous co-precipitation of two compounds having significantly different solubilities in designated washing solutions such that the more soluble compound can be dissolved and removed from the less soluble compound during the washing of the co-precipitated particles. The porous particles then can be coated to change the surface properties if so desired. The porous particles can then be dried to remove almost all moisture from the particles leaving porous particles with lower density. Such particles in dry form can be useful for high strength low weight materials.

Particles which are about one micron diameter or smaller have pores so small that they do not fill rapidly with liquid when the particles are rewetted. In this way it is possible to entrap air (or other gas) in the particles. Such particles can be useful as echogenic ultrasound contrast materials.

An important principle underlying this invention is the differential solubilities of the two compounds chosen for co-precipitation. For example, an ester and the acid from which it is synthesized may both be insoluble in aqueous solutions at, for example, pH 5–7. However, the acid may have significantly higher solubility at pH 10–11 such that washing at basic pH dissolves the acid leaving porous particles consisting solely, or mostly, of the ester compound.

Other acid derivatives, such as amides can be substituted for the ester compound recognizing that the wash solution may have to be at a lower pH to be effective.

Similarly, two compounds could be chosen for washing with an organic solvent as long as the two compounds have significantly different solubilities in that solvent.

This invention can be practiced utilizing compounds which differ in solubility in a given wash solution by orders of magnitude. The difference in solubility, however, can be small—a factor of two or less—but substantially more washing will be required to create the porous particles.

Figure 1:
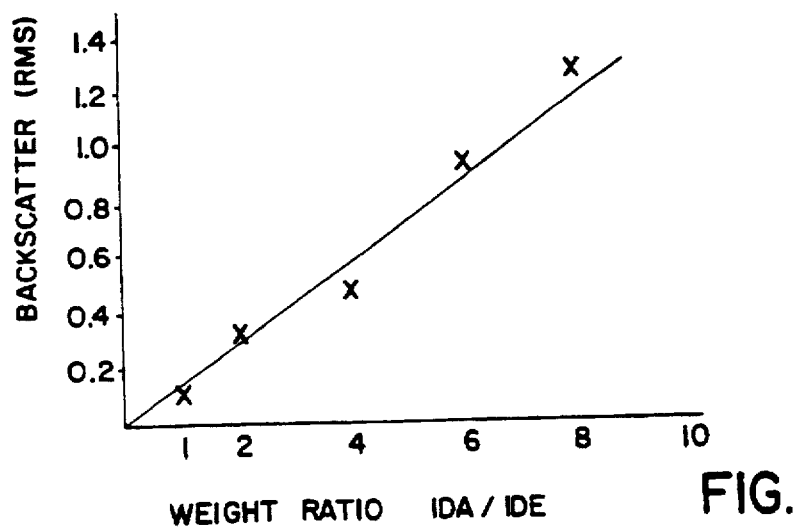

Varying the ratio of more-soluble to less soluble components can alter the properties of the resultant particles. For example, varying the ratio of iodipamic acid (IDA) to iodipamide ethyl ester (IDE) from 2:1 to 8:1 significantly increases the echogenicity of the resultant particles, as shown in FIG. 1. These data illustrated in FIG. 1 was acquired at 4.7 mg/ml.

Figure 2:
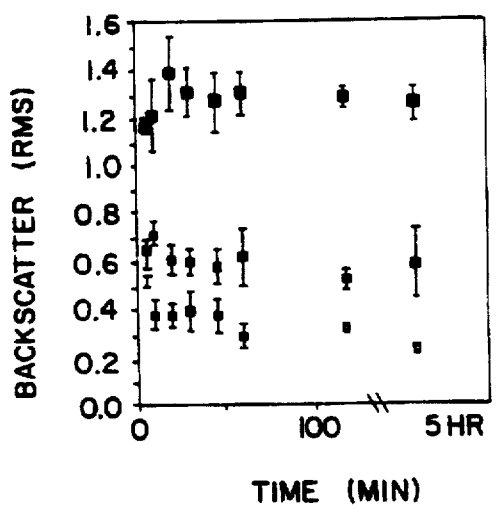

Varying the concentration of particles also affects the echogenic properties of a suspension. As shown in FIG. 2, the RMS backscatter of particles in plasma increased from 0.4 to 1.2 when the concentration of particles increases from 5.2 to 13.1 mg/ml.

The ultrasmall porous particles of the instant invention can be coated with substances to alter their surface properties. For example, coating the particles with serum albumin can improve the biocompatibility of such particles. Coating with antibodies may improve the targeting of particles to a desired site. Coatings altering the wetability, charge, or permeability of the particle surface of such particles may be applied prior to drying to achieve the desired surface characteristic.

Drying can be accomplished by any of a number of techniques known to one skilled in the art. Vacuum, spray, or lyophilization may be utilized depending on the compound(s) and application for these particles.

After drying, the particles can be reconstituted with any liquid in which the particles are not soluble. For ultrasonic contrast agents, the liquid generally will be water or some other suitable aqueous solution. Other liquids may be appropriate for other applications.

The preferred IDE/IDA particles are believed to be useful for diagnostic imaging with both computer tomography (CT) and ultrasound. The iodine in the IDE solid matrix is the effective attenuator for CT while the entrapped air is the effective scatterer for ultrasound. Similar particles could be useful for magnetic resonance imaging as well. This would be possible by reconstituting the dried particles with a liquid containing a paramagnetic material, such as gadolinium chelates. After allowing sufficient time for equilibration of the paramagnetic material into the pores of the particles, the particles could be useful for enhanced magnetic resonance imaging of tissues, e.g. liver, in which the biodistribution of the entrapped paramagnetic material is controlled by the particles rather than the bulk liquid biodistribution. Other combinations, e.g., diagnostic and therapeutic agents, could be utilized in the practice of this invention.

The physical chemical principles thought to be involved in this invention suggest that the free energy of the system is higher when the compound is dissolved in the organic solvent than when the compound exists in the particulate or crystalline state. During precipitation the compound will naturally convert to the crystalline form—the lowest free energy state—unless it is trapped in the metastable particulate form, a condition where its free energy is intermediate between the solution and the crystalline phases. When properly practiced, this invention enables the trapping of the compound in the metastable particle state, precluding transformation to the crystalline state.

The size distribution of particles formed during co-precipitation can be correlated with the time interval between onset and completion of co-precipitation. It is believed that a very short time interval results in the production of uniformly sized particles, while a very long time interval results in a broad particle size distribution. Intermediate conditions produce intermediate particle size distributions.

An important parameter for utilization of this invention is the solubility of the compounds in the precipitating liquid. Thus, compounds having essentially little aqueous solubility, i.e., compounds which have an aqueous solubility of less than one part in ten thousand, may be precipitated in an aqueous solution in order to obtain an excellent yield. Compounds which are more water-soluble can also use an aqueous precipitating liquid. However, the higher the solubility of the compounds, the greater the probability that some of the compounds will dissolve in the aqueous phase and transform to the more stable crystalline state. Also, redissolution in the aqueous phase can lead to a broadening of the particle size distribution. For these reasons, it is preferred that an aqueous precipitating liquid be used for compounds having a water-solubility of less than one part in ten thousand.

It has been found that it is possible to prepare suspensions of compounds which are poorly soluble in aqueous solutions, i.e., have a solubility from about one part per ten thousand to about one part per one hundred which provide excellent yields by using an acceptable precipitating liquid in which the compounds have even less solubility than water. The difference in the solubility of the compounds in water as compared to the precipitating liquid need not be large in order to be significant in terms of yield. In order to make particles of a uniform and predetermined size, a solution of the solid compounds in a suitable solvent is prepared. The solution may be diluted with a non-solvent that does not cause the compounds to precipitate. A precipitating liquid is also prepared, preferably with a surfactant, in sufficient quantity to both co-precipitate the compounds and stabilize the resulting suspension of particles of the compounds against aggregation. The precipitating liquid may be used alone when compounds which do not aggregate are used. The precipitating liquid is infused into the solution in which the compounds are dissolved under carefully controlled conditions, including: the rate of stirring of the organic solution, the rate of infusion of the aqueous solution, the volume of the organic solution and the temperature of the solutions and the suspension. The precipitating liquid may be infused, for example, through a needle of standard gauge.

In investigations of varying parameters to adjust for particle size, three usable relationships were discovered: (1) diluting the solution with more of the non-solvent produces larger particles, and diluting with less of the non-solvent produces smaller particles; (2) higher temperatures of the solution during precipitation produce larger particles, and lower temperatures of the solution during precipitation produce smaller particles; and (3) at a given stirring rate of the organic solution, faster infusion rates of precipitating liquid produce smaller particles while slower infusion rates produce larger particles.

When the co-precipitation is complete, the uniformly sized particles are washed to remove the solvent, i.e. by centrifugation, filtration, etc. and the soluble compound to produce the porous particles of the instant invention. In most cases, the particles should be separated from the solvent quickly to prevent-transformation to a crystalline form.

Aqueous precipitating liquids are useful for many compounds, including but not limited to organic compounds such as iodipamide ethyl ester, iothalamate ethyl ester, iosefamate ethyl ester, 2,2', 4 4'-tetrahydroxybenzophenone, RS nitrocellulose, progesterone, beta-2,4,6-triiodo-3-dimethyl formamidinophenyl propionic acid ethyl ester, N-(trifluoroacetyl) Adrimycin 14 valerate, 1,2 diaminocyclohexane malinate platinum (II), norethisterone, acetyl salicylic acid, wafarin, heparin-tridodecyl methyl ammonium chloride complex, sulfamethoxazole, cephalexin, prednisolone acetate, diazepam, clonazepam, methidone, naloxone, disulfiram, mercaptopurine, digitoxin, primaguine, mefloquine, atropine, scopolamine, thiazide, furosemide, propanalol, methyl methacrylate, poly methyl methacrylate, 5-fluorodeoxyuridine, cytosine arabinoside, acyclovir, and levonorgestrel; and inorganic compounds such as aluminum chloride hexahydrate, the oxides of iron, copper, manganese and tin.

Compounds which are better suited for precipitation using a non-aqueous precipitating liquid include organic compounds such as mitindomide, hydrolytically unstable compounds such as isopropylpyrrolizine (IPP, or carbamic acid, (1-methylethyol)-, (5-(3,4-dichlorophenol)-2,3-dihydro-1,H-pyrrolizine-6-,7-diyl) bis(-methylene ester); and inorganic compounds such as iron citrate, iron iodate, calcium pyrophosphate, calcium salicylate, platinum dichloride and sodium pyrophosphate.

The first step is to prepare a solution of two compounds, one compound being of interest, in a suitable solvent for the compounds. This can occur by simply dissolving the compounds in the solvent of choice.

The solvent is chosen to suit the compounds. For example, dimethylformamide (DMF) is a solvent for iothalamate ethyl ester (IEE) and iosefamate ethyl ester (IFE), and dimethylsulfoxide (DMSO) is a solvent for iodipamide ethyl ester (IDE) and IEE. DMSO is also a suitable solvent for compounds such as mitindomide. Another suitable solvent for many compounds, and especially IPP, is tetrahydrofuran (THF).

The solution is then optionally diluted with a non-solvent that does not cause the compounds to precipitate. The non-solvent causes greater dispersion of the dissolved molecules of the compounds in the liquid phase. Greater dilution of the solution with non-solvent produces larger particles, and less dilution of the solution with non-solvent produces smaller particles.

The non-solvent should not precipitate the compounds when it is added to the solution. Lower aliphatic alcohols, such as ethanol, are effective non-solvents for solutions of IDE and IEE in DMSO. For the ethyl esters of triiodobenzoic acid, proportions of non-solvent to solvent at a ratio of 2 or more can-produce 1 to 3 micron sized particles (depending on other parameters); and ratios of less than 2 can produce submicron particles, at least as applied to DMSO solutions diluted with ethanol.

To co-precipitate the compounds from the solution in a desired particle size, preferably a solution of a surfactant is prepared in sufficient quantity to effect complete precipitation of the compounds and to stabilize the resulting suspension of particles of the compound against aggregation. The surfactant provides the stabilization against aggregation, while a suitable precipitating agent causes the co-precipitation of the compounds. Presence of extra surfactant solution is advisable to ensure stabilization so that the co-precipitated particles suspended in liquid do no aggregate, forming agglomerates of an improperly large size. While surfactants are used in most cases, some compounds appear to form stable, substantially non-aggregated particles without the use of surfactants. Examples of such non-aggregating compounds are certain heparin complexes.

It is thought that particles with relatively high surface charge are less likely to require surfactant in the precipitating solution. The surface charge of a particle is sometimes referred to as its zeta potential, a measurement of charge which falls off with distance. There may be a threshold zeta potential above which no surfactant is needed, but below which, surfactant is needed to keep the precipitating particles from aggregating. The zeta potential is directly correlated with the polarity or net charge of a compound. Thus, the need for surfactant in the precipitating solution may be predicted from the extent of the charge or polarity of the compound employed in the method of the invention. For example, heparin complexes are highly charged, and form stable non-aggregated particles when precipitated with water.

Generally, such a theory notwithstanding, empirical methods will suffice; that is, a co-precipitation may first be performed with water, and if aggregation occurs, then a co-precipitation in the presence of surfactant is indicated. surfactants are chosen for their compatibility with the compounds and their ability to stabilize a suspension of compound particles. For work with IEE and IDE drugs, a solution of 5% polyvinylpyrrolidone (C-30), 0.1% polyvinylpyrrolidone (C-15), or 0.1% human serum albumin is preferred. Also 0.1% Pluronic F-68, [Poloxamer 188, a poly(oxyethylene-co-oxypropylene) polymer], a 0.33% gelatin, 0.33% gelatin plus 0.6% Hetastarch, 0.33% gelatin plus 0.002% propylene glycol, and 0.3% gelatin plus 2% sucrose, or other surfactants known to one skilled in the art can be used.

To co-precipitate particles of the compound in the desired sizes, the precipitating liquid and the solution are combined under controlled conditions of temperature, ratio of infusion rate to stirring rate, and the proportion of non-solvent to solvent in the dispersed solution.

Preferably, the solution being infused with precipitating liquid is agitated. This can be accomplished by stirring, shaking, by the infusion itself and by other techniques known to those skilled-in the art. This effect can also be achieved by combining a stream of precipitating liquid with a stream of the solution.

The co-precipitation of the compounds occurs exothermically, heating the solution and the resulting suspension. The temperature of the solution and resulting suspension is controlled to achieve the particle size of precipitate that is desired. Higher solution temperatures during precipitation produce larger particles, and lower solution temperatures during precipitation produce smaller particles. Since many compounds are less soluble at lower temperatures, it is generally preferred to conduct the infusion of precipitating liquid at a low temperature in order to maximize yield. The lower limit of the temperature at which co-precipitation can be conducted is, of course dependent upon the freezing point of the solvent, precipitating liquid, as well as economic concerns.

Also, faster infusion rates at constant stirring rate of organic solution produce smaller particles, and slower infusion rates produce larger particles.

FIGS. 6–8 show the effects on particle size of varying parameters during precipitation of IDE from a DMSO solution diluted with 1 part solution to 2 parts ethanol using an aqueous solution of 5% polyvinylpyrrolidone at different infusion rates and temperatures.

FIG. 6 shows that as the volume and stirring rate of the organic compound iodipamide ethyl ester and dimethyl sulfoxide/ethanol solution are increased, the infusion rate of aqueous surfactant solution must be increased proportionally as defined by: infusion rate (ml/min.)=23+0.14 [volume (liters)×stir rate (r.p.m.)] to produce particles of 1 micron diameter at 4° C.

FIG. 7 shows that at a constant ratio of infusion rate to [stir rate×volume], increased precipitation temperature produces larger particles.

FIG. 8 plots 3 points for rate of infusion of the precipitating liquid into the organic solution to approximate the curve by which larger particles are formed from slower injection rates, showing that at a constant ratio of temperature to [stir rate×volume], particle side is inversely related to the rate of infusion of the precipitating liquid.

When FIGS. 6–8 are considered together, they show clearly that higher temperatures and slower mixing rates produce larger particles, and lower temperatures and faster mixing rates produce smaller particles. Another parameter than can be varied to affect particle size is the amount of dilution of the solution before co-precipitation occurs.

When the co-precipitation is complete, extra surfactant solution can be added to further stabilize the suspended particles against agglomeration. The extra solution can be added at a rapid rate, since essentially all the compounds are now co-precipitated in uniformly sized particles. The precipitated particles are promptly separated from the solvent to prevent redissolving and reprecipitation of particles at undesirable sizes. Centrifuging is a preferred way to perform the separation. Other methods, including membrane filtration, reverse osmosis, and others known to persons skilled in the art may also be used to remove undesired substances.

Promptly after separating the particles, the particles are washed or rinsed with a solution in which one of the two compounds initially dissolved is soluble to remove solvent and excess surfactant and to remove or extract such solubilized compound from the precipitated particles and dried as discussed hereinabove.

The dried porous particles prepared according to the method outlined above may be resuspended in an appropriate suspension vehicle which may be aqueous or non-aqueous solution, as the situation requires. For example, where the porous particles formed comprise a pharmaceutical compound for parenteral administration, the porous particles are ultimately resuspended in an aqueous solution, such as sterile water. In so doing, however, gas bubbles, such as air bubbles, will be entrapped in the crevices or pores of the particles. In other instances, the particles may be suspended in a carrying agent such as an ointment, gel, or the like. Preferably, the compound has the same range of solubility in the suspension vehicle as in the precipitating liquid.

It should be understood to those versed in this art that the methods and ultrasmall, non-aggregated solid particles disclosed in U.S. Pat. No. 4,826,689 and U.S. Pat. No. 4,997,454, provide teachings upon which the instant invention has improved, and therefore are incorporated herein by reference in their entireties.

Examples of ultrasmall, substantially non-aggregated porous particles of the present invention will now be further illustrated with reference to the following examples.

EXAMPLE I

Ultrasmall, non-aggregated porous iodipamide ethyl ester (IDE) particles having a substantially uniform mean diameter of about 0.5 microns were prepared as recited hereunder and suspended in bovine plasma-distilled water (1:1) solution and placed in a small plastic pipette.

A pulse-echo technique was used to determine relative backscatter. A wide band 10 MHz center frequency, Panametrics transducer (1.3 cm diameter 5 focus), driven by a JSR Pulser, was used to obtain rf scan lines. For in vitro measurements, the mean backscatter (root mean square, RMS) was computed for eight uncorrelated scan lines, each corresponding to about 4 mm in length.

In vitro analysis of the bubble/IDE particle suspension reveals that backscatter increases linearly with concentration, as shown in FIG. 9.

Figure 3:
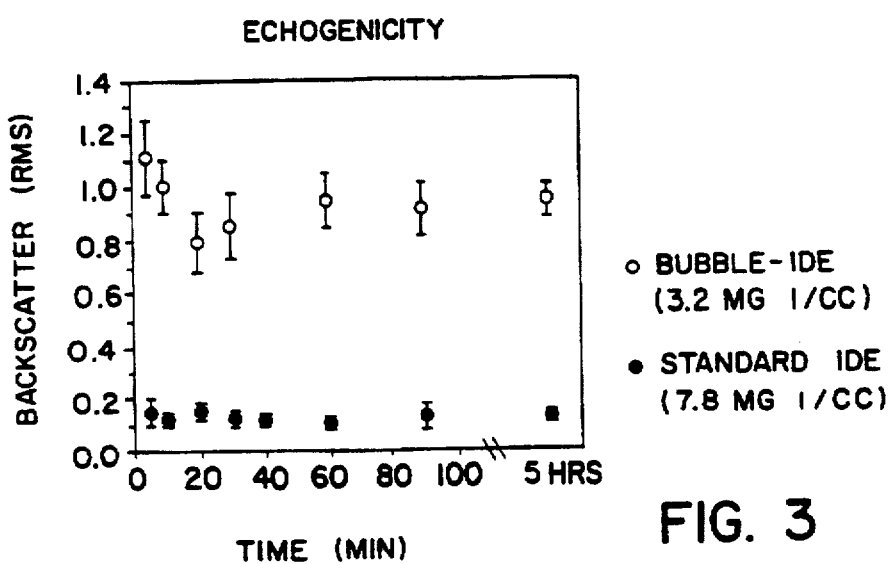

In vitro analysis of the bubble/IDE particle suspension and a standard solid IDE particle suspension after mixing with bovine plasma, reveals a much higher backscatter from the bubble/IDE particles than from the solid IDE particles, as shown in FIG. 3. Moreover, these data demonstrate that the high echo-genicity of the bubble/IDE particles is sustained for hours after mixing with bovine-plasma.

To prepare the bubble/IDE suspension, about 250 mg of solid iodipamide ethyl ester (IDE) and 500 mg of iodipamic acid (IDA) were added to a 50 ml beaker with 1"×5/16" teflon coated stir bar. Approximately 5 mls of dimethylsulfoxide (DMSO) were added and stirred for about 10–15 min. until dissolved. To the solution, approximately 6.25 mls of absolute ethanol were added. The beaker was then cooled in an acetone/dry ice bath. While cooling, the mixture was stirred quickly, but without splashing. Approximately 4.5 mls of water at about pH 5 in about 0.5 ml increments were slowly injected into the mixture while maintaining the temperature thereof at about 0° C. Approximately 8 mls of water at about pH 5 was then infused into the mixture at a rate of about 5 mls/min. starting at about 0° C. Thus, a total of 12.5 mls of water was infused into the mixture. A Harvard Infusion pump and a 60 cc plastic syringe and 19 gauge infusion set (butterfly) were used to infuse the water. Co-precipitation occurred after about 6.5 mls of water were infused into the mixture and at a temperature of about 1° C. Following co-precipitation, the suspension was stabilized by adding about 150 mls of 1% polyvinylpyrrolidone (PVP) at about pH 7.4 and kept at a temperature of about 10° C. The suspension was then poured into a 250 ml centrifuge bottle (approximately 31.25 mls) and centrifuged at approximately 2500 rpm for about 30 min. The supernate was discarded. The precipitate in the centrifuge bottle was then washed with approximately 31.25 mls of about 0.1% PVP at about pH 11 until the wash reached a pH of about 10 to extract the IDA from the IDE particles to generate the ultrasmall, non-aggregated, porous, non-crystalline IDE particles. The particles where then treated with human serum albumin according to Example III and then lyophyllized according to the procedure set forth in Example IV.

EXAMPLE II

New Zealand white rabbits (Hazelton Laboratories) weighing 2–4 Kg were anesthetized, and injected intravenously at a rate of about 1 ml/min. with a 8–10 ml (depending on rabbit weight) suspension of iodipamide ethyl ester (IDE) porous particles having a substantially uniform mean diameter of about 0.5 microns. The final concentration of the bubble/IDE particle suspension was approximately 100 mg/ml. The injected dose of the bubble/IDE particle suspension was approximately 250 mg IDE/Kg rabbit body weight. The IDE particles contained air bubbles trapped within their crevices or pores.

Figure 4:
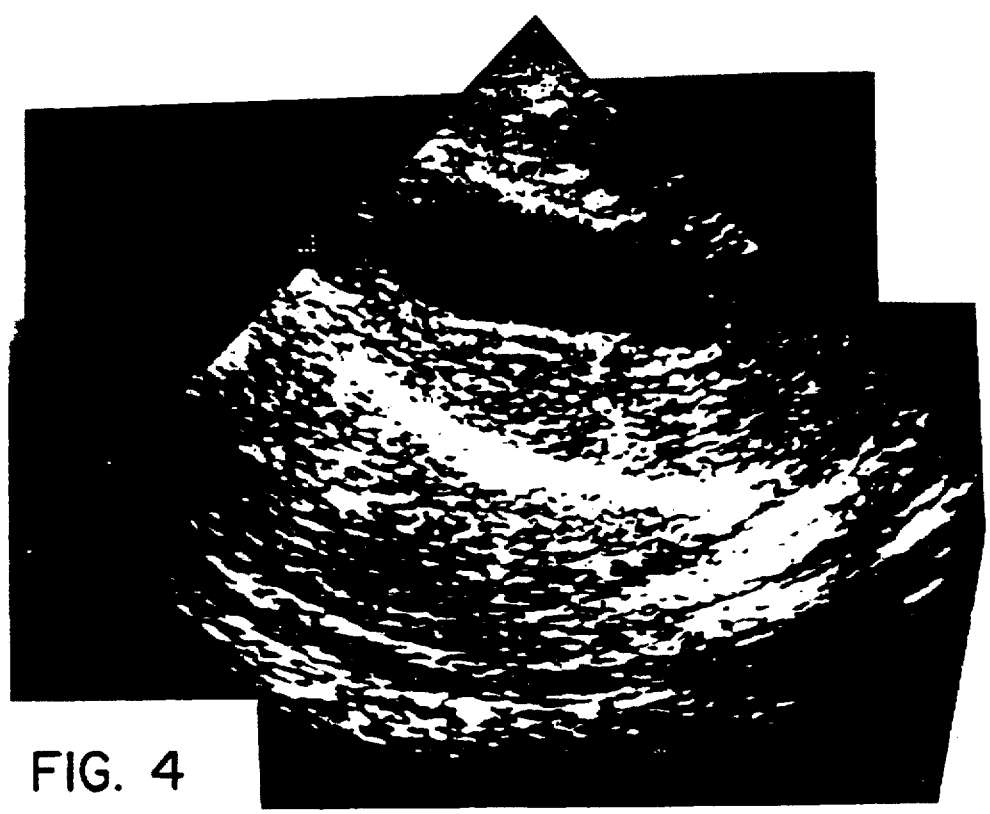
FIG. 4 depicts B-scan image at 5 MHz of normal rabbit liver with gall bladder before infusion of the bubble/IDE contrast agent.
Figure 5:
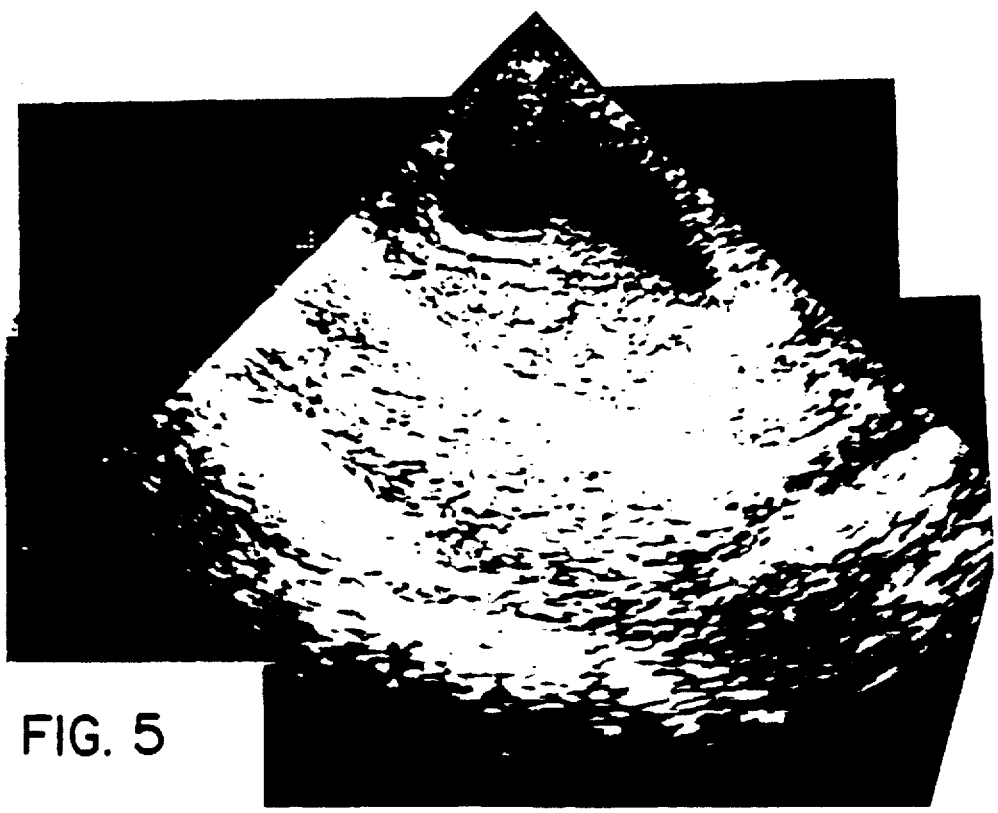
FIG. 5 depicts B-scan image at 5 MHZ of normal rabbit liver with gall bladder, but 60 minutes following intravenous infusion of the bubble/IDE contrast agent. The enhancement of the parenchymal echogenicity was observed for at least 120 minutes after contrast administration.

The rabbits were scanned periodically. B-scan images of rabbit liver with and without the bubble/IDE particle suspension are shown in FIGS. 4 and 5. These images were obtained from a 5.0 MHz Acuson Scanner with all settings held constant over a 120 min. examination.

Liver echogenicity following intravenous administration of the bubble/IDE particle suspension is markedly enhanced as compared with no contrast agent, as evidenced by FIGS. 4 and 5. Results in these rabbits demonstrate that the stabilized/echo-genic gas can be delivered to the liver, raising the backscatter well above the levels obtained with no contrast agent or with standard solid IDE particles. Improving liver lesion detection by enhanced ultrasound may now be possible with the bubble/IDE particles.

To prepare the bubble/IDE particle suspension, about 5000 mg of solid iodipamide ethyl ester (IDE) and about 10,000 mg of iodipamic acid (IDA) were added to a 800 ml beaker with 2"×⅝" teflon coated stir bar. Approximately 100 mls of dimethylsulfoxide (DMSO) were added and stirred for about 10–15 min. until dissolved. To the solution, approximately 125 mls of absolute ethanol were added. The beaker was then cooled in an acetone/dry ice bath. While cooling, the mixture was stirred quickly, but without splashing. Approximately 90 mls of water at about pH 5 at about 10 ml increments were slowly injected into the mixture while maintaining the temperature thereof at about 0° C. Approximately 160 mls of water at about pH 5 was then infused into the mixture at a rate of 100 ml/min. starting at about 0° C. Thus, a total of 250 mls of water was infused into the mixture. A Harvard Infusion pump and a 60 cc plastic syringe and 19 gauge infusion set (butterfly) were used to infuse the water. Co-precipitation occurred after about 125 mls of water were infused into the mixture and at a temperature of about 2° C. Following co-precipitation, the suspension was stabilized by adding 150 mls of about 1% polyvinylpyrrolidone (PVP) at about pH 7.4 and kept at a temperature at about 10° C. The suspension was then poured into five 250 ml centrifuge bottles (approximately 125 ml per bottle) and centrifuged at approximately 2500 rpm for about 30 min. The supernate was discharged. The precipitates remaining in the five centrifuge bottles were then washed with approximately 125 mls of about 0.1% PVP at about pH 11 until the wash reached a pH of about 10 to extract the IDA from the particles and to form the ultrasmall, non-aggregated, porous, non-crystalline IDE particles. The particles were then treated with human serum albumin according to Example III and then lyophyllized according to the procedure set forth in Example IV.

EXAMPLE III

The IDE particles of Examples I and II were coated with human serum albumin to improve the biocompatibility of such particles.

To coat the IDE particles, an appropriate amount of the IDE suspension (e.g. 250 mg or 5 g) is pipetted into a 50 ml centrifuge tube. The tube is centrifuged at 2500 rpm for 30 min. Mix thoroughly with a vortex mixer. To 5 g or 250 mg of the IDE porous particles, add 100 mls or 5 mls, respectively, of about 25% human serum albumin (HSA) and mix thoroughly with vortex mixer. A preferred HSA/IDE ratio in accordance with the instant invention is about 5:1. Let the HSA mixture stand at room temperature for about two hours. After standing, mix thoroughly with a vortex mixer approximately every 30 min., and then store at room temperature overnight. Centrifuge the stored mixture at about 3000 rpm for 120 min. Discard supernate. Add by pipette, approximately 2.0 mls for 250 mg of IDE or 15 mls for 5 g of IDE of about 0.1% PVP at about pH 7.4 and mix thoroughly with vortex mixture.

EXAMPLE IV

To lyophilize the IDE particles of Examples I or II, place centrifuge tubes in dry ice/acetone bath to freeze suspension as quickly as possible. To facilitate a thin frozen layer, the suspension may be rolled onto the lower sides of the centrifuge tube. Once frozen, place frozen tubes in lyophilizer as quickly as possible and begin lyophilization. Typical lyophilizer settings include: freeze-dryer temperature equal about −55° C.; shelf temperature is equal to about −40° C.; and vacuum is at about 10–50 micrometer mercury. The frozen suspension should be lyophilized until the moisture remaining is about 2% or less. When removing from the lyophilizer, immediately cap the centrifuge tubes and store in a refrigerator at about −5° C. until needed.

The present invention may, of course, be carried out in other specific ways than those herein set forth without departing from the spirit and essential characteristics of the invention. The present embodiments are, therefore, to be considered in all respects as illustrative and not restrictive and all changes coming within the mean and equivalency range o the appended claims are intended to be embraced therein.

Having described our invention, we claim:

1. A porous particle preparation produced by the process comprising:

(a) preparing a solution which includes first and second solid compounds in a suitable solvent;

(b) infusing a precipitating liquid into the solution, the two solid compounds having low solubility in the precipitating liquid, so as to produce a suspension of co-precipitated substantially non-aggregated particles of a uniform size; and (c) washing the particles in a suitable washing liquid, the first and second compounds having differential solubility in the washing liquid such that the first compound has a lower solubility than the second compound in said washing liquid, so that at least some of the second compound is selectively extracted from the first compound to produce porous particles having a porous matrix.

2. A porous particle preparation according to claim 1, wherein the mean particle diameter is selected from the range of from about 0.01 microns to about 5.0 microns.

3. A porous particle preparation according to claim 1, wherein the mean particle diameter is selected from the range of from about 0.1 microns to about 2.0 microns.

4. A porous particle preparation according to claim 1, wherein the particle size distribution has a maximum relative standard deviation of about 30%.

5. A method of forming porous particles comprising:

(a) preparing a solution which includes first and second compounds in a suitable solvent;

(b) infusing a precipitating liquid into the solution, the two compounds having a low solubility in the precipitating liquid, so as to produce a suspension of co-precipitated substantially non-aggregated particles of a uniform size; and (c) washing the particles in a suitable washing liquid, the first and second compounds having differential solubility in the washing liquid such that the first compound has a lower solubility in the washing liquid than the second compound, so that the second compound is selectively extracted from the first compound to produce a porous matrix.

6. A method according to claim 5 including the further step of separating the co-precipitated particles from the solvent.

7. A method according to claim 5, wherein additional precipitating liquid is added to the suspension before the particles are washed.

8. A method according to claim 6, wherein the particles are separated by centrifugation, membrane filtration, or reverse osmosis.

9. A method according to claim 5, wherein the precipitating liquid is a surfactant solution.

10. A method according to claim 5, wherein a solution is prepared such that the concentrations of the two solid compounds are near their solubility limits in the solvent.

11. A method according to claim 5, wherein the first solid compound is iodipamide ethyl ester and the second solid compound is iodipamic acid, the solvent is DMSO, the precipitating liquid is water at a pH of about 5.0, and the washing liquid is an aqueous solution of polyvinylpyrrolidone at a pH of about 11.

12. The method according to claim 5, wherein the weight ratio of the second compound to the first compound in the co-precipitated particles is in the range of from about 2:1 to about 10:1.

13. A method according to claim 5 including the further step of drying said porous particles.

14. A method according to claim 5 including the further step of coating said porous particles.

15. A method according to claim 5 including the further step of suspending the porous particles in a liquid.

16. The method of claim 5, wherein the porous particles are non-crystalline.

17. The method of claim 5, wherein the infusing step is performed at a temperature below room temperature and an infusion rate of from about 0.01 ml/min. to about 3000 ml/min. per 50 ml unit volume of solution.

18. The method of claim 5, wherein the size of the particles ranges up to about 10 microns.

19. The method of claim 5, wherein the size of the particles is directly related to the solution temperature during precipitation and inversely related to the infusion rate.

20. The method of claim 6, wherein the separating step is before the washing step.

21. The method of claim 5, wherein the amount of the second compound removed during washing is about 10% to about 100%.

22. The method of claim 5, wherein the solubility differential between the first and second compound is at least about a factor of two.

23. The method of claim 5, wherein the solubility differential between the first and second compound is at least about an order of magnitude.

24. The method of claim 5, further comprising the step of entrapping gas within the porous matrix.

25. The method of claim 5, further comprising suspending the particles in a pharmaceutically acceptable carrier.

26. The method of claim 5, wherein the precipitating liquid comprises a surfactant.

27. The method of claim 26, wherein the surfactant is selected from the group consisting of polyvinylpyrrolidone (C-30), polyvinylpyrrolidone (C-15), human serum albumin, Pluronic F-68 (Poloxamer 188, a poly (oxyethylene-co-oxypropylene)polymer), a gelatin, gelatin plus Hetastarch, gelatin plus propylene glycol, and gelatin plus sucrose and combinations.

28. The method of claim 5, wherein the first compound is an ester or an amide, the second compound is the acid from which it is synthesized, and the washing liquid is a base.

29. The method of claim 5, wherein the solubility of the first and second compounds is between about 1 in 10,000 and 1 in 100 in the precipitating liquid.

30. Particles produced by the process of claim 5.

31. The particles of claim 30, the particles having a pharmaceutically acceptable uniform diameter and having a plurality of pores able to trap gas for an extended period when the particles are placed in a liquid.

32. The particles of claim 30, wherein the particles have the ability to enhance ultrasound back scatter as a result of entrapped gas when used as an ultrasound contrast agent.

33. In a method of making uniformly sized particles of a solid compound comprising preparing a solution of the solid compound in a solvent, infusing a precipitating liquid into the solution so as to produce a suspension of precipitated uniformly sized particles of the solid compound, the improvement comprising:

(a) co-dissolving a first and a second solid compound in a solvent for the two compounds;

(b) infusing a co-precipitating liquid so as to co-precipitate particles of the first and second compounds;

(c) selectively extracting at least some of the second compound from the co-precipitated particles in an extractive washing liquid in which the first and second compounds have differential solubility so as to produce porous particles having a porous matrix of the first compound; and (d) recovering the porous particles.

* * * * *